(12) United States Patent
Chmura

(10) Patent No.: US 8,845,663 B2
(45) Date of Patent: Sep. 30, 2014

(54) BILIARY DECOMPRESSION AND ANASTOMOSIS STENT

(71) Applicant: Cook Medical Technologies LLC, Bloomington, IN (US)

(72) Inventor: Kevin Chmura, Lewisville, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 13/720,334

(22) Filed: Dec. 19, 2012

(65) Prior Publication Data

US 2013/0110141 A1     May 2, 2013

Related U.S. Application Data

(62) Division of application No. 12/575,982, filed on Oct. 8, 2009, now abandoned.

(51) Int. Cl.
*A61B 17/11*     (2006.01)
*A61F 2/04*     (2013.01)

(52) U.S. Cl.
CPC ............. *A61B 17/11* (2013.01); *A61B 17/1114* (2013.01); *A61B 2017/1139* (2013.01)
USPC ........................................ 606/153; 623/23.64

(58) Field of Classification Search
USPC .............................. 606/153; 623/23.64–23.65
See application file for complete search history.

(56) References Cited

U.S. PATENT DOCUMENTS

| 2,308,484 | A | 1/1943 | Auzin et al. |
| 3,771,526 | A | 11/1973 | Rudie |
| 3,908,646 | A | 9/1975 | Ansari |
| 3,986,493 | A | 10/1976 | Hendren, III |
| 4,294,255 | A | 10/1981 | Geroc |
| 4,294,362 | A | 10/1981 | Martensson |
| 4,619,247 | A | 10/1986 | Inoue et al. |
| 4,790,809 | A | 12/1988 | Kuntz |

(Continued)

FOREIGN PATENT DOCUMENTS

| EP | 1 493 391 A1 | 1/2005 |
| EP | 1 600 121 A | 11/2005 |

(Continued)

OTHER PUBLICATIONS

Cope, C. et al.; "Stent placement of gastroenteric anastomoses formed by magnetic compression"; Journal of Vascular and Interventional Radiology, vol. 10, Issue 10; Abstract; 1999.

(Continued)

*Primary Examiner* — Suzette J Gherbi
(74) *Attorney, Agent, or Firm* — Brinks Gilson & Lione

(57) ABSTRACT

A stent and a method for implanting a stent for decompression and anastomosis formation are provided. The stent includes a non-expandable, generally tubular body having a proximal portion and a distal portion, a lumen extending through at least a portion of the body, a distal opening in the distal portion in fluid communication with the lumen and a proximal opening in the proximal portion in fluid communication with the lumen. The stent further includes a first magnetic element positioned on the distal portion of the tubular body and a second magnetic element movably positionable on the proximal portion of the tubular body. The second magnetic element is configured to surround and move over the proximal portion of the tubular body towards the first magnetic element.

20 Claims, 8 Drawing Sheets

(56) References Cited

U.S. PATENT DOCUMENTS

| | | |
|---|---|---|
| 4,865,030 A | 9/1989 | Polyak |
| 4,873,977 A | 10/1989 | Avant et al. |
| 4,957,479 A | 9/1990 | Roemer |
| 4,978,323 A | 12/1990 | Freedman |
| 4,989,299 A | 2/1991 | Morita |
| 5,176,626 A | 1/1993 | Soehendra |
| 5,334,208 A | 8/1994 | Soehendra et al. |
| 5,425,763 A | 6/1995 | Stemmann |
| 5,429,131 A | 7/1995 | Scheinman et al. |
| 5,466,242 A | 11/1995 | Mori |
| 5,514,176 A | 5/1996 | Bosley, Jr. |
| 5,643,277 A | 7/1997 | Soehendra et al. |
| 5,647,843 A | 7/1997 | Mesrobian et al. |
| 5,681,260 A | 10/1997 | Ueda et al. |
| 5,690,656 A | 11/1997 | Cope et al. |
| RE35,849 E | 7/1998 | Soehendra |
| 5,800,517 A | 9/1998 | Anderson et al. |
| 5,876,450 A | 3/1999 | Johlin, Jr. |
| 5,997,573 A | 12/1999 | Quijano et al. |
| 6,258,098 B1 | 7/2001 | Taylor et al. |
| 6,352,543 B1 | 3/2002 | Cole |
| 6,632,229 B1 | 10/2003 | Yamanouchi |
| 6,652,540 B1 | 11/2003 | Cole et al. |
| 6,652,569 B1 | 11/2003 | Taylor et al. |
| 6,699,263 B2 | 3/2004 | Cope |
| 6,719,768 B1 | 4/2004 | Cole et al. |
| 6,802,847 B1 | 10/2004 | Carson et al. |
| 6,932,827 B2 | 8/2005 | Cole |
| 6,985,776 B2 | 1/2006 | Kane et al. |
| 7,241,300 B2 | 7/2007 | Sharkawy et al. |
| 7,282,057 B2 | 10/2007 | Surti et al. |
| 7,544,203 B2 | 6/2009 | Chin et al. |
| 7,572,290 B2 | 8/2009 | Yodfat et al. |
| 7,771,442 B2 | 8/2010 | Shriver |
| 7,775,967 B2 * | 8/2010 | Gertner ........................ 600/37 |
| 7,909,837 B2 | 3/2011 | Crews et al. |
| 7,938,841 B2 | 5/2011 | Sharkawy et al. |
| 8,066,725 B2 | 11/2011 | Copa et al. |
| 8,211,186 B2 | 7/2012 | Belhe et al. |
| 8,221,505 B2 | 7/2012 | Skerven |
| 2001/0004699 A1 | 6/2001 | Gittings et al. |
| 2001/0032010 A1 | 10/2001 | Sandock |
| 2001/0047180 A1 | 11/2001 | Grudem et al. |
| 2002/0082614 A1 | 6/2002 | Logan et al. |
| 2002/0143389 A1 | 10/2002 | St. Pierre |
| 2003/0130610 A1 | 7/2003 | Mager et al. |
| 2003/0139703 A1 | 7/2003 | Burkett et al. |
| 2004/0034377 A1 | 2/2004 | Sharkawy et al. |
| 2005/0080439 A1 | 4/2005 | Carson et al. |
| 2005/0192603 A1 | 9/2005 | Cole et al. |
| 2006/0253133 A1 | 11/2006 | Ortiz |
| 2007/0233170 A1 * | 10/2007 | Gertner ........................ 606/192 |
| 2007/0250084 A1 | 10/2007 | Sharkawy et al. |
| 2008/0051626 A1 | 2/2008 | Sato et al. |
| 2008/0097493 A1 | 4/2008 | Copa et al. |
| 2008/0114384 A1 | 5/2008 | Chang et al. |
| 2008/0208314 A1 | 8/2008 | Skerven |
| 2009/0036872 A1 * | 2/2009 | Fitzgerald et al. ........... 604/533 |
| 2009/0048618 A1 | 2/2009 | Harrison et al. |
| 2009/0082778 A1 | 3/2009 | Beane et al. |
| 2009/0093822 A1 | 4/2009 | Ducharme |
| 2009/0125042 A1 | 5/2009 | Mouw |
| 2009/0227828 A1 * | 9/2009 | Swain et al. ................... 600/12 |
| 2010/0036399 A1 | 2/2010 | Viola |
| 2010/0163054 A1 * | 7/2010 | Breznel et al. ................ 128/831 |
| 2011/0087252 A1 | 4/2011 | Chmura |
| 2012/0035628 A1 | 2/2012 | Aguirre et al. |

FOREIGN PATENT DOCUMENTS

| | | |
|---|---|---|
| EP | 1 894 514 A2 | 3/2008 |
| WO | WO 81/00668 | 3/1981 |
| WO | WO 03/103541 A | 12/2003 |
| WO | WO 2008/061024 A2 | 5/2008 |

OTHER PUBLICATIONS

International Search Report completed Jan. 7, 2011 for International Application No. PCT/US2010/051567.

Written Opinion completed Jan. 7, 2011 for International Application No. PCT/US2010/051567.

* cited by examiner

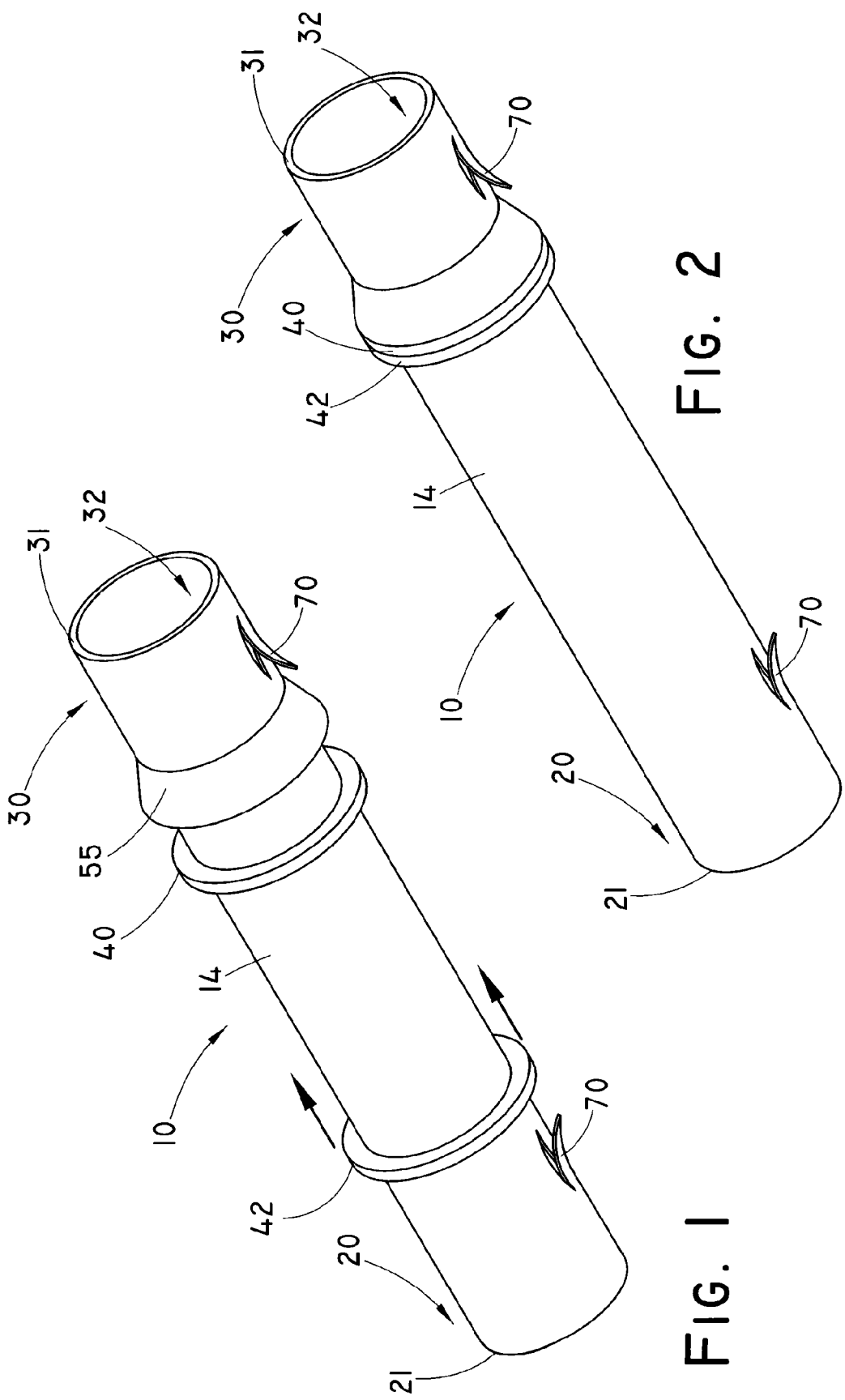

BILIARY DECOMPRESSION AND ANASTOMOSIS STENT

RELATED APPLICATIONS

This application is a division of U.S. application Ser. No. 12/575,982, filed Oct. 8, 2009, which is incorporated by reference herein in its entirety.

TECHNICAL FIELD

The invention generally relates to methods and devices for decompression and for forming an anastomosis between two viscera, and more particularly relates to methods and devices including stents and magnets.

BACKGROUND

Historically, gastro-intestinal (GI) surgery has been performed to create a channel or anastomosis between two viscera for the purpose of redirecting bodily fluids. For example, intestinal contents or bile may be redirected in patients who have developed an obstruction of the bowel or bile duct due to such conditions as tumors, ulcers, inflammatory strictures or trauma. During surgery to form an anastomosis, the two tissues are often brought together using devices such as sutures, staples, or some other fixation means such as adhesives. While the tissues are being brought together during the procedure, various types of surgical instruments may be used to temporarily hold the tissues in place. In open surgery, the temporary holding may be accomplished with graspers, forceps, or other tissue holding instruments that are manipulated by clinicians. In laparoscopic surgery, similar instruments may be used, except that the laprotic access limits the number of instruments that may be inserted into the site making the tissue securing procedure much more challenging.

When these types of GI surgery are performed, there exists the potential to breech the mural boundary. Thus, extreme care must be taken to prevent contamination of the pleural and abdominal cavities with GI contents, which are laden with bacteria that do not naturally occur in those locations. If significant contamination occurs, then serious infection can set in, which can lead to serious illness or death if not treated early and vigorously.

To address these limitations and to minimize the invasiveness of such surgeries, magnetic anastomosis devices (MADs) have been developed for forming anastomoses. An exemplary MAD is disclosed in U.S. Pat. No. 5,690,656, the disclosure of which is incorporated herein by reference in its entirety. Generally, the MAD of the '656 patent includes first and second magnet assemblies including magnetic cores that are surrounded by thin metal rims. The first and second magnet assemblies are positioned in the two viscera between which the anastomosis is desired and brought into close proximity to each other. Due to the magnetic attraction between the two magnetic cores, the walls of the two adjacent viscera are compressed between the magnet assemblies and in particular the magnetic rims, resulting in ischemic necrosis of the walls to produce an anastomosis between the two viscera.

MADs may be delivered through surgical intervention such as laparotomy, over a wire guide using a pushing catheter (and typically under fluoroscopy), by simply swallowing the magnet assemblies of the MAD and using massage under fluoroscopy to align the two magnet assemblies, or endoscopically using grasping forceps. Within about ten days after the visceral tissues surrounding the magnets fuse together, and the magnets and entrapped necrotic tissue subsequently detach from the surrounding tissue to leave an opening between the viscera.

In some patients, the obstruction may cause painful restriction of fluid flow through a body passage that requires a more immediate opening than is typically provided with the MADs. For example, the flow of bile from the liver may be obstructed through the bile duct due to a tumor or other blockage. There exists a need to rapidly restore the fluid flow to release the bile from the duct. Typically, a blockage in the common bile duct can be alleviated by inserting a drainage stent through the Ampula of Vader into the common bile duct to create an opening through the obstruction. However, drawbacks may arise when using a drainage stent inserted through the Ampula of Vader, including obstruction of the drainage stent. In addition, drainage stents periodically need to be changed to maintain the passage and fluid flow out of the bile duct, requiring additional patient procedures.

There is a need for devices and methods for immediate decompression of a duct and subsequent anastomosis.

SUMMARY OF THE INVENTION

Accordingly, it is an object of the present invention to provide a method and a stent having features that resolve or improve on one or more of the above-described drawbacks.

The foregoing object is obtained in one aspect of the present invention by providing a stent for decompression and anastomosis formation. The stent includes a non-expandable, generally tubular body having a proximal portion and a distal portion, a lumen extending through at least a portion of the body; a distal opening in the distal portion in fluid communication with the lumen, and a proximal opening in the proximal portion in fluid communication with the lumen, the body being configured to be disposed at least partially within an internal bodily duct and facilitate the passage of bodily fluid therethrough. The stent further includes a first magnetic element positioned on the distal portion of the tubular body, the first magnetic element having an opening formed therethrough so that the first magnetic element surrounds a portion of the tubular body, and a second magnetic element movably positionable on the proximal portion of the tubular body, the second magnetic element having an opening formed therethrough so that the second magnetic element is configured to surround and move over the proximal portion of the tubular body towards the first magnetic element.

In another aspect of the present invention, a method for forming an anastomosis between two body cavities is provided. The method includes providing an opening through a wall of a first bodily cavity and a second bodily cavity and inserting a stent through the opening. The stent includes a non-expandable, generally tubular body having a proximal portion and a distal portion, a lumen extending through at least a portion of the body; a distal opening in the distal portion in fluid communication with the lumen, and a proximal opening in the proximal portion in fluid communication with the lumen. The stent further includes a first magnetic element positioned on the distal portion of the tubular body, the first magnetic element having an opening formed therethrough so that the first magnetic element surrounds a portion of the tubular body. The method further includes positioning the first magnetic element and the distal portion within the second bodily cavity and positioning the proximal portion within the first bodily cavity so that the lumen is in fluid communication between the first bodily cavity and the second bodily cavity, and then placing the second magnetic element over the proximal portion so that the second magnetic element is movable towards the first magnetic element.

In another aspect of the present invention, a method for forming an anastomosis between two body cavities is provided. The method includes inserting a delivery device through a wall of a first bodily cavity and a wall of a second bodily cavity and delivering a stent over the delivery device to position the stent between the first bodily cavity and the second bodily cavity and to establish fluid flow therebetween. The stent includes a non-expandable, generally tubular body having a proximal portion and a distal portion, a lumen extending through at least a portion of the body; a distal opening in the distal portion in fluid communication with the lumen, and a proximal opening in the proximal portion in fluid communication with the lumen and a first magnetic element positioned on the distal portion of the tubular body, the first magnetic element having an opening formed therethrough so that the first magnetic element surrounds a portion of the tubular body. The method further includes positioning the stent with the proximal portion extending into the first bodily cavity and the distal portion extending into the second bodily cavity, the first magnetic element being positioned in the second bodily cavity on the distal portion, delivering the second magnetic element to the proximal portion of the stent, and creating an anastomosis using the attraction forces of the first magnetic element and the second magnetic element.

BRIEF DESCRIPTION OF THE DRAWINGS

FIG. 1 is a perspective view of a stent according to the present invention showing the magnetic elements spaced apart;

FIG. 2 is a perspective view of the stent according to the present invention with the magnetic elements contacting each other;

DETAILED DESCRIPTION OF THE EMBODIMENTS

Figure 3:
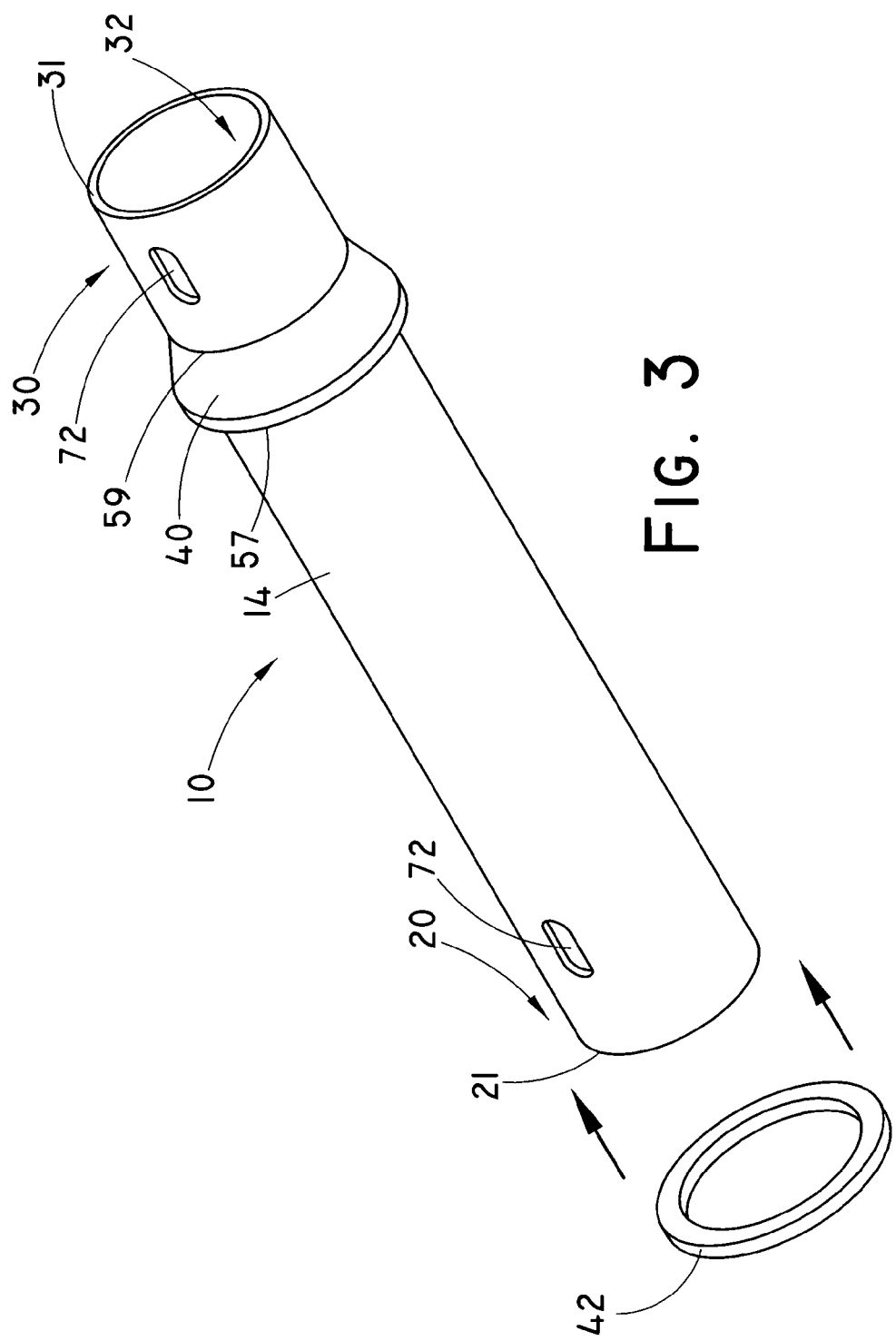
FIG. 3 is a perspective view of the stent according to the present invention with a magnetic element removed from the stent.

The invention is described with reference to the drawings in which like elements are referred to by like numerals. The relationship and functioning of the various elements of this invention are better understood by the following detailed description. However, the embodiments of this invention are not limited to the embodiments illustrated in the drawings. It should be understood that the drawings are not to scale, and in certain instances details have been omitted which are not necessary for an understanding of the present invention, such as conventional fabrication and assembly.

As used in the specification, the terms proximal and distal should be understood as being in the terms of a physician delivering the stent to a patient. Hence the term "distal" means the portion of the stent that is farthest from the physician and the term "proximal" means the portion of the stent that is nearest to the physician.

FIGS. 1 and 2 illustrate a stent 10 in accordance with embodiments of the present invention. The stent 10 includes a non-expandable, generally tubular body 14 having a proximal portion 20 and a distal portion 30. A lumen 32 extends through at least a portion of the tubular body 14 of the stent 10 between a proximal opening 21 and a distal opening 31. The stent 10 further includes a first magnetic element 40 and a second magnetic element 42. The first magnetic element 40 is positioned distal to the second magnetic element 42 on the stent 10. The second magnetic element 42 is movably positionable over the proximal portion 20 of the stent 10. In some embodiments, the first magnetic element 40 is fixed in position on the stent 10. The stent 10 may also include a stopping member 55 to prevent the first magnetic element 40 from moving further distally toward the distal end of the stent 10. As shown in FIG. 3, the second magnetic element 42 is configured to be positioned over the proximal portion 20 of the stent 10 and moved distally towards the first magnetic element 40 and eventually connect to the first magnetic element 40 to form an anastomosis as described in more detail below. The attractive force between the first magnetic element 40 and the second magnetic element 42 will draw the magnetic elements 40, 42 together. As shown in FIG. 3, the second magnetic element 42 is configured to move distally so that the second magnetic element 42 is drawn to toward the magnetic element 40 over the tubular body 14 of the stent 10. FIG. 3 also illustrates a distal end portion 56 that is conically shaped to facilitate insertion of the first magnetic element 40 into a bodily location.

The first magnetic element 40 and the second magnetic element 42 may have any shape and size that allows for the magnetic elements 40, 42 to be positioned on a tubular stent 10 and to allow at least the second magnetic element 42 to move distally toward the first magnetic element 40. The first and second magnetic elements 40, 42 may also be self centering, although the stent 10 also helps to position the first and second magnetic elements 40, 42 for mating. In some embodiments, the first and second magnetic elements 40, 42 may be shaped to nest together to form the anastomosis.

Figure 4:
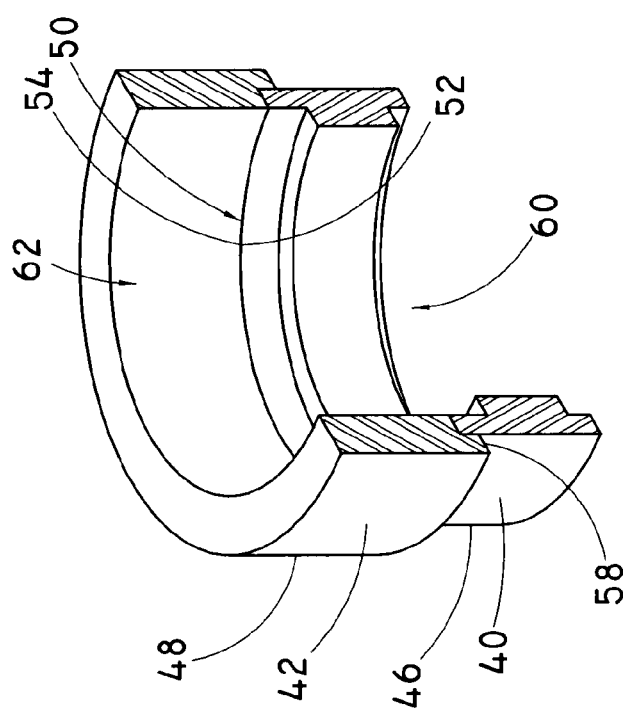
FIG. 4 is a partial view of an embodiment of the magnetic elements according to the present invention.

An exemplary view of the first magnetic element 40 and the second magnetic element 42 is shown in FIG. 4 without the stent is shown to illustrate the mating of the magnetic elements 40, 42. The first magnetic element 40 and the second magnetic element 42 are disc shaped with the first magnetic element 40 having a smaller outer diameter 46 that nests within the outer diameter 48 of the second magnetic element 42. A contacting interface 50 is formed when the first magnetic element 40 contacts the second magnetic element 42 at a first contacting face 52 of the first magnetic element 40 and a second contacting face 54 of the second magnetic element 42. The second magnetic element 42 may include an overlapping rim 58 that extends at least partially over a portion of the first magnetic element 40. When the magnetic elements 40, 42 are implanted within the body, tissue is pressed between the first contacting face 52 and the second contacting face 54 of the first and second magnetic elements 40, 42 as the magnetic elements 40, 42 move closer together to form the anastomosis. The first and second magnetic elements 40, 42 may be formed having atraumatic surfaces that are exposed to the tissue to inhibit irritation within the body as the magnetic elements move closer together and form the anastomosis.

Figure 5:
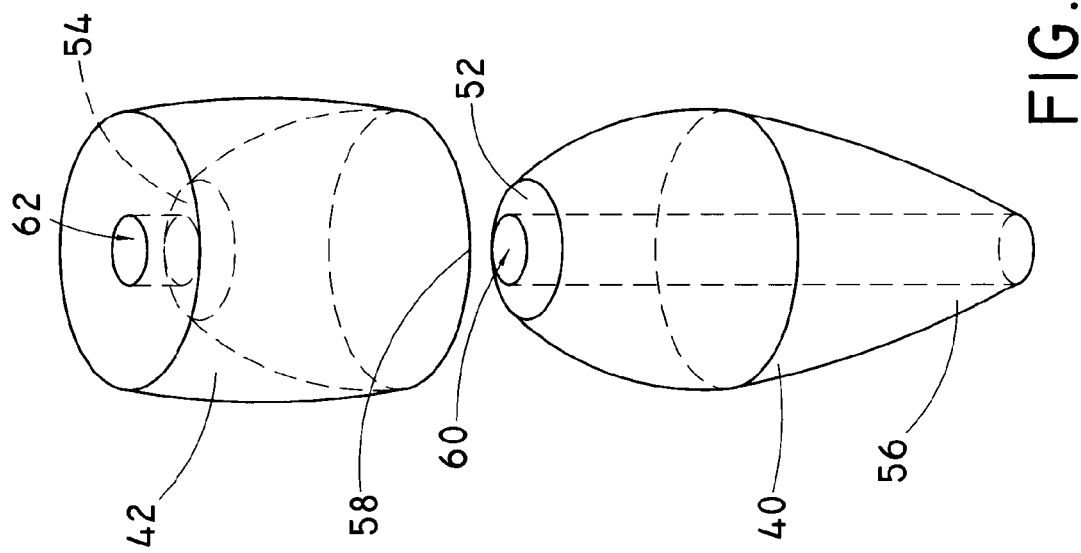
FIG. 5 is a partial view of an alternative embodiment of the magnetic elements according to the present invention.

FIG. 5 illustrates alternative shapes for the first magnetic element 40 and the second magnetic element 42 where the first magnetic element 40 includes a bullet-shaped first contacting face 52 and the second magnetic element 42 is shaped to mate with the first magnetic element 40 and the second contacting face 54 is shaped to mate with bullet-shaped first contacting face 52. One skilled in the art will recognize that many alternative shapes are possible for the magnetic elements 40, 42. In addition, the first magnetic element 40 may include a distal end portion 56 that is shaped to facilitate insertion of the first magnetic element 40 into a bodily location. By way of non-limiting example, the first magnetic element 40 may be tapered at the distal end portion 56 or the entire magnetic element 40 may be tapered from a proximal end 57 to a distal end 59. Although one skilled in the art will recognize that any shape maybe used for either of the magnetic elements 40, 42.

As shown in FIGS. 4 and 5, the first magnetic element 40 includes an opening 60 formed through the magnetic element 40 that is sized and shaped to surround the distal portion 30 of the tubular body 14. The first magnetic element 40 may be secured to the stent 10 so that the first magnetic element 40 is fixed in position in relation to the stent 10 and the second magnetic element 42 moves in relation to the stent 10 and the first magnetic element 40. The first magnetic element 40 may be fixed to the stent 10 using any means known to one skilled in the art, for example, with an adhesive. The second magnetic element 42 includes an opening 62 formed through the magnetic element 42 that is sized and shaped to surround the tubular body 14 of the stent 10 and to be movable over the stent 10 distally toward the first magnetic element 40.

The stent 10 may also include one or more modifications to help retain the stent 10 in position within the bodily location. For example, as shown in FIGS. 1 and 2, one or more retaining members 70 may be included on the tubular body 14. The retaining member 70 may be a flap that extends a length of about 4-8 mm from the tubular body 14. Other lengths for the retaining member may be possible and may depend on the size of the duct opening, the flexibility of the retaining member, the length of the stent and the amount of time the stent 10 is to remain implanted within the duct. The retaining member 70 may be formed from the tubular member 14 with a longitudinal cut in the wall of the tubular member 14. Alternatively, the retaining member 70 may be formed by molding with the body 14 or addition to the tubular body 14 or any method known to one skilled in the art. One or more openings 72 may be included in the tubular body 14 as shown in FIG. 3. The openings 72 are configured to facilitate drainage through the stent 10. Additional modifications such as one or more pigtails may also be included on the stent 10. The first magnet 40 may also be shaped to help retain the stent 10 in position against the ductal wall.

The stent 10 may be of any size suitable for implantation into a bodily duct and will vary depending on the size of the duct. The stent 10 may have an outer diameter of about 3-15 Fr. The length of the stent may be 5-30 cm. Shorter or longer stents may also be used. These sizes are merely exemplary and other sizes may be used.

The stent may be made from materials so that the stent is soft enough to conform to the curvature of the duct and eliminate or reduce irritation at the implantation site that occurs with a rigid stent, thus reducing the risk of irritation, morphological or ductal changes. The materials should also have sufficient strength to maintain a lumen through the stent when the stent is positioned within the duct. Exemplary materials for the stent 10 include, but are not limited to the following, SOF-FLEX™, a type of polyether urethane, silicone, block co-polymers, urethanes, polyethylene, polystyrene, polytetrafluoroethylene (PTFE), FEP and the like and combinations thereof. In some embodiments, the stent 10 may be formed from biodegradable materials. A number of bioabsorbable homopolymers, copolymers, or blends of bioabsorbable polymers are known in the medical arts. These include, but are not necessarily limited to, polyesters including poly-alpha hydroxy and poly-beta hydroxy polyesters, polycaprolactone, polyglycolic acid, polyether-esters, poly (p-dioxanone), polyoxaesters; polyphosphazenes; polyanhydrides; polycarbonates including polytrimethylene carbonate and poly(iminocarbonate); polyesteramides; polyurethanes; polyisocyantes; polyphosphazines; polyethers including polyglycols polyorthoesters; expoxy polymers including polyethylene oxide; polysaccharides including cellulose, chitin, dextran, starch, hydroxyethyl starch, polygluconate, hyaluronic acid; polyamides including polyamino acids, polyester-amides, polyglutamic acid, poly-lysine, gelatin, fibrin, fibrinogen, casein, collagen.

The magnetic elements may be formed from any material having magnetically attractable materials. As used herein, magnetic refers to all magnetically attractable materials, such as magnets and magnetically charged members, as well as ferrous materials such as iron, nickel cobalt, steel and various alloys that are attractable to a magnet. For example the magnets may be rare-earth magnets, such as Neodymium-iron-boron, cobalt, etc. Although the first and second magnetic elements have been depicted as magnets, it will be recognized by one skilled in the art that only one of the magnetic elements may be a magnet where the other magnetic element is a ferrous material or other material that is simply attracted to the one magnet. The magnetic elements may also include a protective coating to protect the magnetic elements from the potentially corrosive effects of the bodily fluids. By way of non-limiting example, the magnetic elements may be coated with a polymeric coating such as parylene, polyesters, polyurethanes, polyethylenes, polyamides, and silicone. The coating may also be formed of various metals or alloys, such as TEFLON and PARALENE® and the like.

Figure 6:
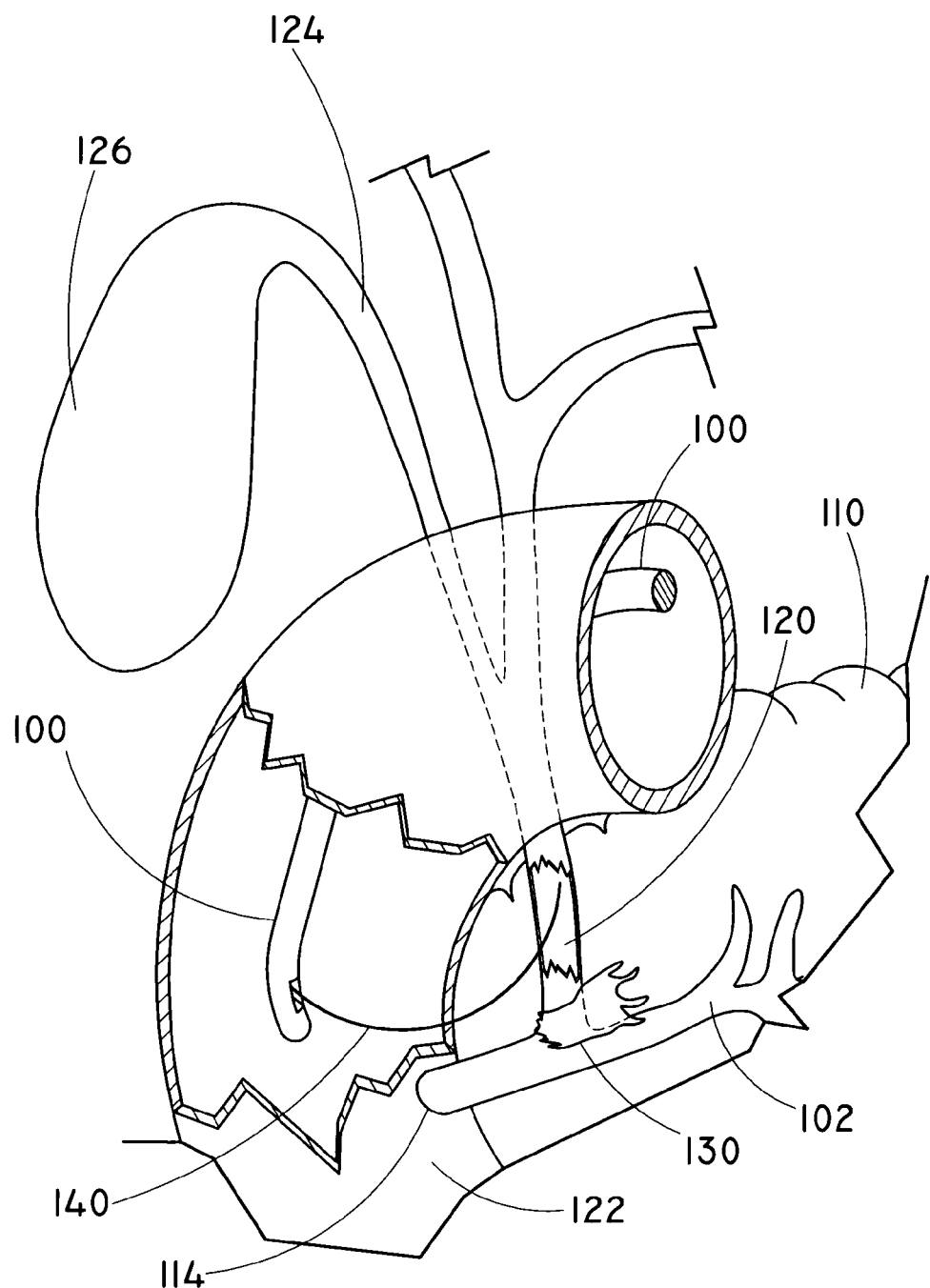
FIG. 6 is a diagrammatic view of a delivery system within the GI tract for placement of the stent.

An exemplary method of delivering and implanting the stent 10 of the present invention will be illustrated with reference to the delivery system 100. By way of non-limiting example, a method of forming an anastomosis between the common bile duct and the duodenum is shown. One skilled in the art will understand that an anastomosis may be formed between other ducts and the duodenum or other portions of the GI tract using the stent and the magnetic elements of the present invention. As shown in FIGS. 6-10, the delivery system 100 may be used to place the stent 10 in the common bile duct 120. With reference to FIG. 6, the relative positions of several organs of the abdominal cavity are shown, including the pancreatic duct 102 of the pancreas 110, the duodenum 122, the cystic duct 124 and the gall bladder 126. A mass 130 is also shown obstructing the opening of the common bile duct 120 and thus blocking fluid flow out of the common bile duct.

Figure 7:
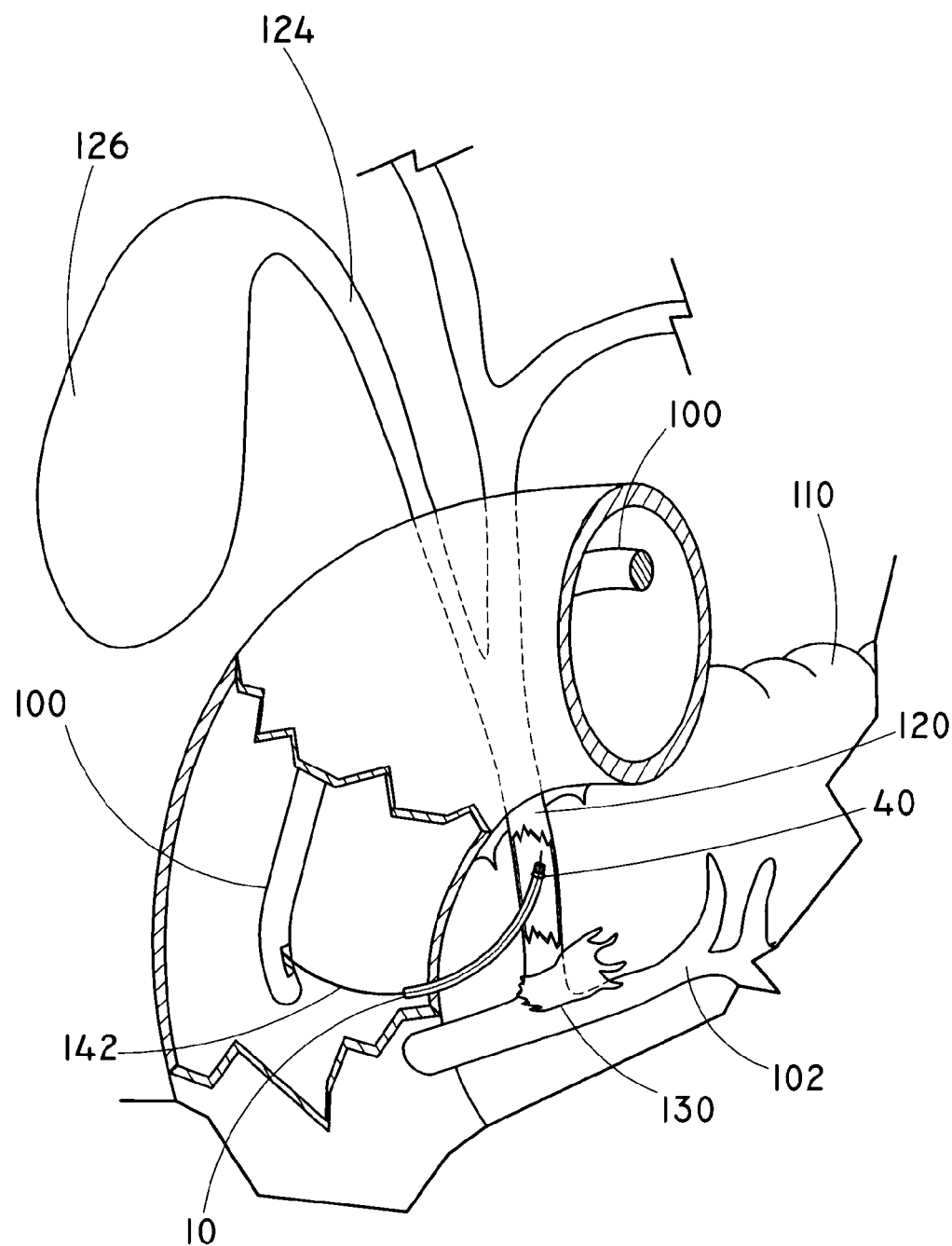
FIG. 7 is a diagrammatic view of the placement of the stent between the common bile duct and the duodenum.

As shown in FIG. 6, the delivery system 100, typically an endoscope or an endoscopic ultrasound (EUS) device that utilizes high frequency sound waves to create an image of living tissue or an echogenic surface, is positioned in the duodenum 122. An EUS device 100 is shown in FIG. 6 having a needle 140 extending from the EUS device 110 and through the wall of the duodenum 122 and through the wall of the common bile duct 120. As shown in FIG. 7, the stent 10 is being delivered over a wire guide 142 that has been inserted through the walls of the duodenum 122 and the common bile duct 120. The distal end portion 30 of the stent 10 is positioned in the common bile duct 120 so that the first magnetic element 40 is positioned within the common bile duct 120. The stent 10 extends between the common bile duct 120 and the duodenum 122 creating opening via the lumen 21 of the stent 10 for fluid to flow out of the common bile duct 120 into the duodenum 122 providing immediate decompression of the biliary blockage.

Figure 8:
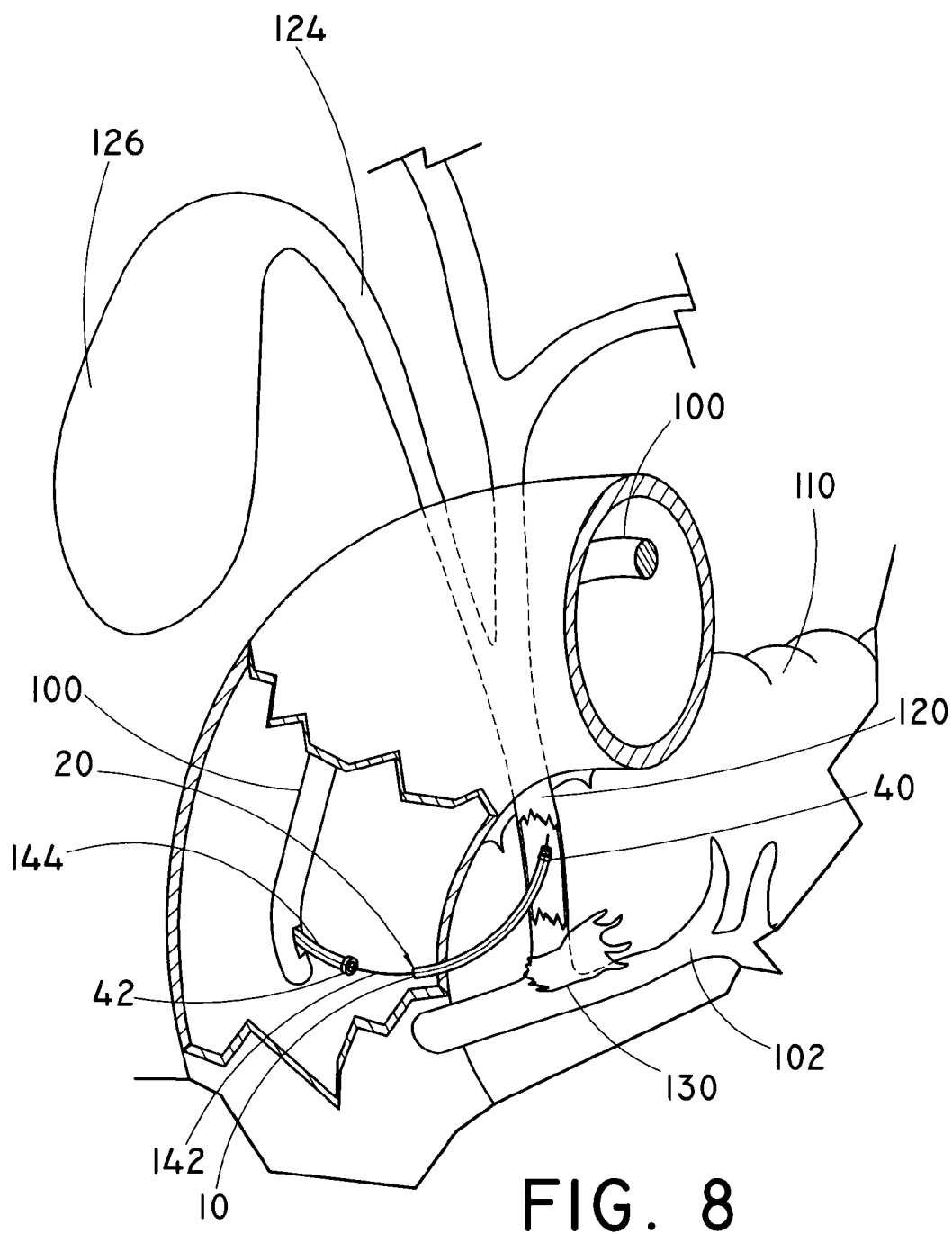
FIG. 8 is a diagrammatic view of the placement of the second magnetic element onto the stent within the duodenum.

As shown in FIG. 8, the second magnetic element 42 may be delivered to the stent 10 using the same delivery system 100. Alternatively, as will be understood by one skilled in the art, a second delivery system may be used to place the second magnetic element 42 of the proximal end 20 of the stent 10. As shown in FIG. 8, a pushing catheter 144 may be used to push the magnetic element 42 into position on the stent 10 over the wireguide 110. Similarly, alternative types of introducer catheters may be used to deliver the second magnetic element 42 into position on the stent 10 within the duodenum 122.

Figure 9:
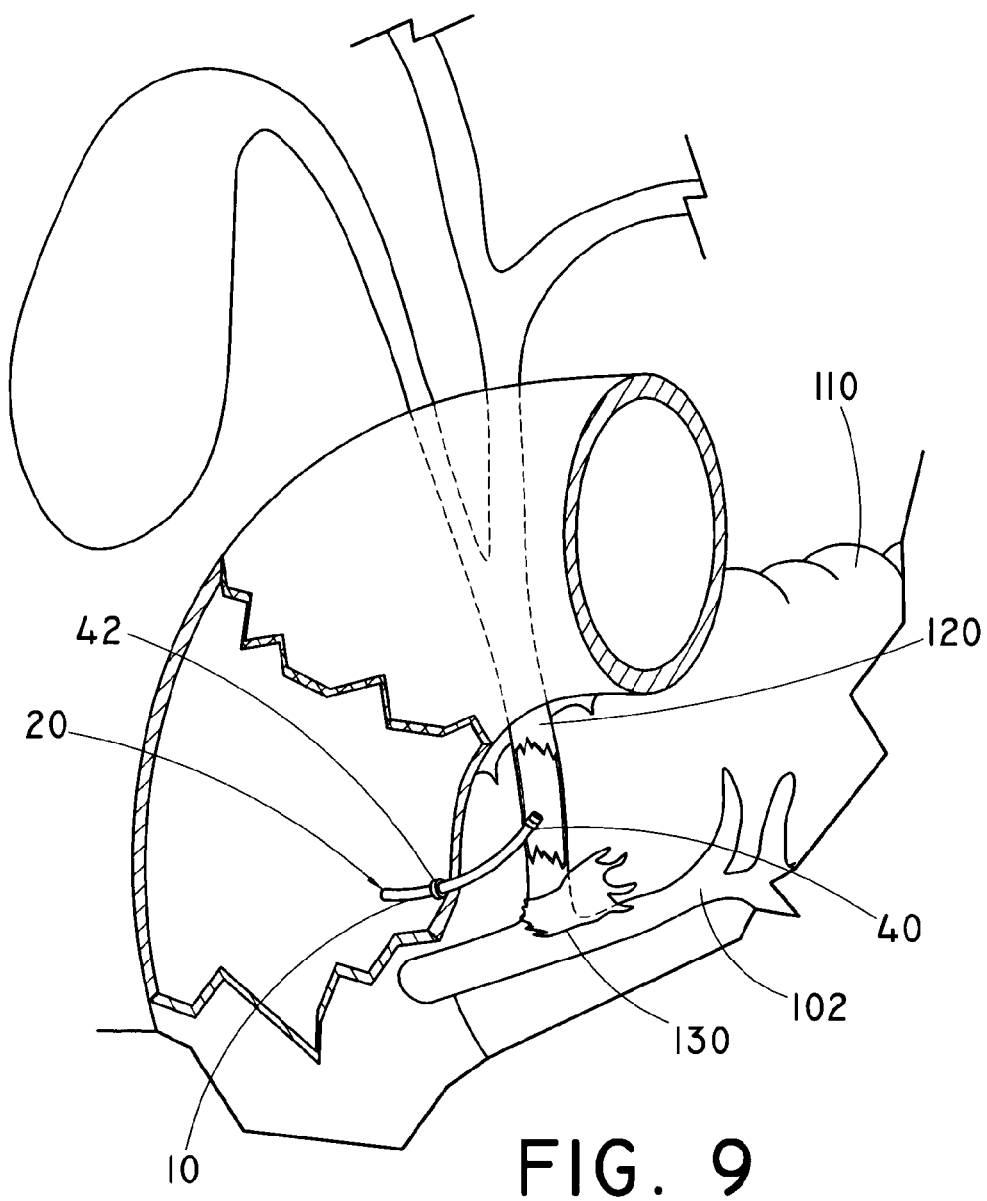
FIG. 9 is a diagrammatic view of the second magnetic element moving distally towards the first magnetic element on the stent.

FIG. 9 illustrates the stent 10 in position and forming the opening for fluid flow out of the common bile duct 120 and into the duodenum 122. The second magnetic element 42 is movably positioned over the proximal end portion 20 of the stent 10 and is advancing towards the magnetic element 40. The attractive force between the first magnetic element 40 and the second magnetic element 42 is sufficient to prevent the second magnetic element form falling off of the stent 10, for example during movement of the GI tract. The stent 10 may also include a protrusion 70 proximal to the position of the second magnetic element 42 that also helps to prevent release of the magnetic element 42 from the stent 10. The arrows shown in FIG. 8 indicate the direction of movement of the second magnetic element 42 towards the first magnetic element 40 that also brings the wall of the duodenum 122 into proximity with the wall of the common bile duct 120.

Figure 10:
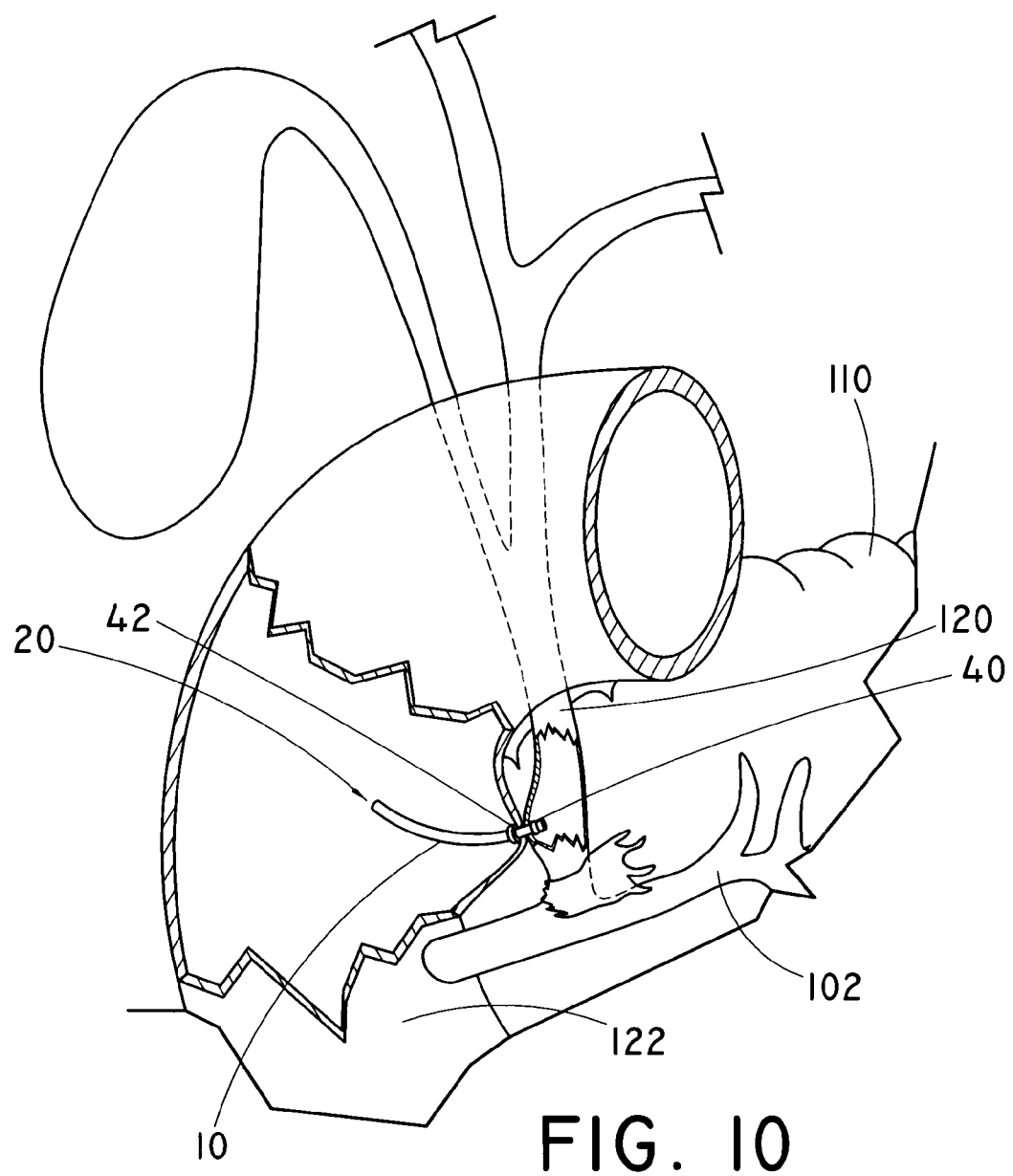
FIG. 10 is a diagrammatic view of the second magnetic element contacting the first magnetic element.

FIG. 10 illustrates the joining of the second magnetic element 42 to the first magnetic element 40 on the stent 10. The tissue between the first and second magnetic elements 40, 42 dies and necroses to form an anastomosis between the duodenum 122 and the common bile duct 120 to create a permanent opening for drainage of the fluid from the common bile duct 20. The anastomosis may be created within about 10 days. Eventually, the stent 10 and the first and second magnetic elements 40, 42 fall out of the opening and pass naturally though the GI system. The stent 10 with the magnet elements 40, 42 preferably passes without additional intervention by the physician, such as would be required to replace a stent that has been inserted into the common bile duct 120 through the Ampula of Vader 114.

The stent 10 may also be placed between the common bile duct 120 and the duodenum 122 using a delivery system 100 using an alternative entry position. The delivery system 100 may be positioned in the duodenum 122 and a wireguide 142 is inserted into the common bile duct 120 through the Ampula of Vader 114. An ECRP endoscope may be used to access the common bile duct 120 in the event that the obstruction prevents the wireguide 142 from entering the common bile duct. The wireguide 142 or the needle 140 may be inserted into the common bile duct 120 and through the walls of both the common bile duct 120 and the duodenum 122. The stent 10 may be inserted over the wire guide through the common bile duct 120 and out of the holes through the walls of the common bile duct and the duodenum so that the proximal portion of the stent 10 extends in the duodenum. The first magnetic element is placed within the common bile duct 120 with the distal end portion 30 of the stent 10. The second magnetic element 42 is advanced over the proximal end portion 20 of the stent 10 as described above.

The above Figures and disclosure are intended to be illustrative and not exhaustive. This description will suggest many variations and alternatives to one of ordinary skill in the art. All such variations and alternatives are intended to be encompassed within the scope of the attached claims. Those familiar with the art may recognize other equivalents to the specific embodiments described herein which equivalents are also intended to be encompassed by the attached claims. For example, the invention has been described in the context of the biliary system for illustrative purposes only. Application of the principles of the invention to any other bifurcated lumens or vessels within the body of a patient, including areas within the digestive tract such as the pancreatic system, as well as areas outside the digestive tract such as other vascular systems, by way of non-limiting examples, are within the ordinary skill in the art and are intended to be encompassed within the scope of the attached claims.

The invention claimed is:

1. A method for forming an anastomosis between two body cavities, the method comprising:
    providing an opening through a wall of a first bodily cavity and a second bodily cavity;
    inserting a stent through the opening; the stent comprising:
        a non-expandable, generally tubular body having a proximal portion and a distal portion, a lumen extending through at least a portion of the body; a distal opening in the distal portion in fluid communication with the lumen, and a proximal opening in the proximal portion in fluid communication with the lumen; and
        a first magnetic element positioned on the distal portion of the tubular body, the first magnetic element having an opening formed therethrough so that the first magnetic element surrounds a portion of the tubular body;
    positioning the first magnetic element and the distal portion within the second bodily cavity and positioning the proximal portion within the first bodily cavity so that the lumen is in fluid communication between the first bodily cavity and the second bodily cavity; and
    placing the second magnetic element over the proximal portion so that the second magnetic element is movable towards the first magnetic element.

2. The method of claim 1, further comprising advancing the second magnetic element distally toward the first magnetic element using the attractive forces between the first and second magnetic elements to advance the second magnet.

3. The method of claim 1, further comprising compressing a portion of the wall of the first bodily cavity and a portion of the wall of the second bodily cavity between the first and second magnetic elements to create an anastomosis.

4. The method of claim 1, further comprising delivering the second magnetic element using an introducer catheter.

5. The method of claim 1, comprising providing the opening through the walls of the first and second bodily cavities using a needle device.

6. The method of claim 5, comprising inserting the needle using an endoscopic ultrasound device.

7. The method of claim 1, wherein the first magnetic element is placed into a common bile duct and the second magnetic element is placed into the duodenum.

8. The method of claim 7, wherein positioning the stent between the common bile duct and the duodenum provides immediate decompression of the biliary blockage.

9. The method of claim 1, wherein the stent is positioned in the opening over a wireguide.

10. A method for forming an anastomosis between two body cavities, the method comprising:

inserting a delivery device through a wall of a first bodily cavity and a wall of a second bodily cavity;

delivering a stent over the delivery device to position the stent between the first bodily cavity and the second bodily cavity and to establish fluid flow therebetween; the stent comprising:

a non-expandable, generally tubular body having a proximal portion and a distal portion, a lumen extending through at least a portion of the body; a distal opening in the distal portion in fluid communication with the lumen, and a proximal opening in the proximal portion in fluid communication with the lumen; and a first magnetic element positioned on the distal portion of the tubular body, the first magnetic element having an opening formed therethrough so that the first magnetic element surrounds a portion of the tubular body;

positioning the stent with the proximal portion extending into the first bodily cavity and the distal portion extending into the second bodily cavity, the first magnetic element being positioned in the second bodily cavity on the distal portion;

delivering the second magnetic element to the proximal portion of the stent; and creating an anastomosis using the attraction forces of the first magnetic element and the second magnetic element.

11. The method of claim 10, wherein the stent is removable and fluid flow is established through the anastomosis.

12. The method of claim 11, wherein the stent is removable without further surgical intervention.

13. The method of claim 10, wherein the stent is delivered over a wireguide.

14. A method for forming an anastomosis between two body cavities, the method comprising:

creating a first opening through a wall of a first bodily cavity and a second opening through a wall of a second bodily cavity;

inserting a non-expandable stent through the first and second openings so that the first bodily cavity is in fluid connection with the second bodily cavity through a lumen of the stent; the stent having a first magnetic element positioned on a distal portion of the stent, the first magnetic element having an opening formed therethrough so that the first magnetic element surrounds a portion of the stent; and positioning the first magnetic element and the distal portion within the second bodily cavity and positioning a proximal portion of the stent and the second magnetic element within the first bodily cavity.

15. The method of claim 14, wherein the second magnetic element is positioned over the proximal portion after the proximal portion is positioned within the first body cavity.

16. The method of claim 14, wherein the second magnetic element is delivered to the stent using a pushing catheter to position the second magnetic element on the proximal portion of the stent.

17. The method of claim 14, wherein the fluid connection between the first and second bodily cavities provides immediate decompression of a blockage in the first bodily cavity or the second bodily cavity.

18. The method of claim 14, comprising creating an anastomosis using the attraction forces of the first magnetic element and the second magnetic element.

19. The method of claim 18, wherein the second magnetic element is movable towards the first magnetic element to create anastomosis.

20. The method of claim 14, wherein the stent is removably positioned.

* * * * *